United States Defensive Publication [19] (H) [11] T966,008

Williams [43] Jan. 3, 1978

[54] OXIDATION OF p-XYLENE TO TEREPHTHALALDEHYDE

[76] Inventor: James E. Williams, 139 Deadrick St., Kingsport, Tenn. 37663

[21] Appl. No.: 752,230

[22] Filed: Dec. 20, 1976

Related U.S. Application Data

[63] Continuation of Ser. No. 611,380, Sept. 8, 1975.

[51] Int. Cl.[2] ..... C07C 45/02

[52] U.S. Cl. ..... 260/599

[57] ABSTRACT

Terephthalaldehyde is produced by the vapor phase oxidation of p-xylene in the presence of a catalyst mixture of tungsten in the form of an oxide or silicotungstic acid, molybdenum in the form of an oxide and bismuth in the form of an oxide, wherein the activity of the catalyst is prolonged by contacting the catalyst mixture intermittently or continuously with molybdenum oxide vapor or a compound which forms molybdenum oxide under the reaction conditions.

4 Claims, No Sheets Drawing,

11 Pages Specification

The file of this unexamined application may be inspected and copies thereof may be purchased (849 O.G. 1221, Apr. 9, 1968).